(12) United States Patent
Araujo

(10) Patent No.: US 7,856,746 B1
(45) Date of Patent: Dec. 28, 2010

(54) TAG CLIP FOR LABELING TUBES, CABLES AND THE LIKE

(76) Inventor: Luis Araujo, 3 Catherine La., Carver, MA (US) 02330

( * ) Notice: Subject to any disclaimer, the term of this patent is extended or adjusted under 35 U.S.C. 154(b) by 113 days.

(21) Appl. No.: 12/317,453

(22) Filed: Dec. 23, 2008

(51) Int. Cl.
*G09F 3/00* (2006.01)
(52) U.S. Cl. .............................. 40/316; 24/487; 24/543
(58) Field of Classification Search .................. 40/316; 24/487, 543; 248/68.1
See application file for complete search history.

(56) References Cited

U.S. PATENT DOCUMENTS

| | | | | |
|---|---|---|---|---|
| 4,669,688 A | * | 6/1987 | Itoh et al. ................... | 248/74.2 |
| 4,881,705 A | * | 11/1989 | Kraus ......................... | 248/74.2 |
| 5,535,969 A | * | 7/1996 | Duffy, Jr. .................... | 248/68.1 |
| 5,613,655 A | * | 3/1997 | Marion ....................... | 248/68.1 |
| 5,815,894 A | * | 10/1998 | Soriano ....................... | 24/510 |
| 5,820,048 A | * | 10/1998 | Shereyk et al. ............. | 248/68.1 |
| 6,561,465 B2 | * | 5/2003 | Kondo ........................ | 248/74.3 |
| 7,124,471 B2 | * | 10/2006 | Koessler ..................... | 16/267 |
| 2005/0116122 A1 | * | 6/2005 | Nakanishi ................... | 248/68.1 |
| 2005/0178930 A1 | * | 8/2005 | Yon ........................... | 248/68.1 |
| 2005/0284989 A1 | * | 12/2005 | Mizukoshi ................... | 248/65 |
| 2007/0018057 A1 | * | 1/2007 | Kovac ........................ | 248/68.1 |
| 2007/0215757 A1 | * | 9/2007 | Yuta ........................... | 248/68.1 |

* cited by examiner

*Primary Examiner*—Gary C Hoge

(57) ABSTRACT

A tag clip is disclosed having a first and second section, the second section having a channel therein for securing a tube or wire. The channel includes resilient support arms extending inward from the channel sides which flex inward upon the forced entry of a tube or wire into the channel. The clip first section folds over and is secured onto the clip second section, pushing the tube or wire into the channel, further flexing the resilient support arms inward with minimal deformation of the tube or cable therein. The equal and opposite forces provided by the first section contact with the tube and the resiliency of the flexible arms allow the tag to be secured to the tube or wire while at the same time allow for the tag to be moved into different positions along the length of the wire or tube. The tag has a rigid molded plastic member that provides the medical personnel or health care providers a substantially stiff or hard surface so that they can write legibly thereon.

10 Claims, 8 Drawing Sheets

TAG CLIP FOR LABELING TUBES, CABLES AND THE LIKE

BACKGROUND OF THE INVENTION

1. Field of the Invention

The present invention relates to a label apparatus for labeling tubes, Cables, Wires, Conduits and the like, and in particular to a tag or label apparatus for use with a tube of a fluid delivery system, such as that used in intravenous infusion and hemodynamic monitor transducer systems.

2. Description of Related Art

Various different forms of strips and bands including identifying and/or or other indicia thereon heretofore have been provided for securement about and/or support from a midportion of an elongated member. However, this inventor has not heard of previous devices that allow for a tube or cable to be labeled and at the same time minimizing any constricting of the tube or cable by the labeling device. In applications involving fluid delivery systems, the present invention allows for minimal tube deflection while simultaneously providing a label disposed in a manner such that the identifying tag will be maintained stationary on the tube, independent of vertical or horizontal orientation or vibration of the tube. The tube systems for delivering fluid medicaments (including gasses), the use of which would benefit from the identification of the tubes or their fluids, comprise tubes in a multitude of diameters. The heretofore described labeling apparatus is adaptable for adherence to such tube systems without restriction to fluid flow.

A principal means for delivering fluid medicaments to a patient in a hospital, clinic, operation, or emergency situation is through the use of an intravenous (IV) infusion system or drip bag (IV pumps, pressure infuser bag, or gravity driven drip). These systems include a fluid-containing elevated bag with a tube connected to and in fluid communication with the bottom of the bag. The other end of the tube may be in fluid communication with a needle or insertion apparatus a portion of which is inserted intravenously in the patient, or may be in fluid communication with a pump apparatus that monitors the flow of a plurality of fluids and directs the plurality of fluids into a patient intravenously.

A variety of fluids are administered to patients. In addition, an individual patient may receive a plurality of fluids simultaneously. Often, each fluid-containing bag is detachably connected by a clear, plastic tube to a flow-monitoring apparatus through a plurality of inlets on the apparatus, also known as the manifold. The bags containing the multiple fluids are often hung from a stand so that the fluids flow, or are assisted, by force of gravity, or fluid flow may be facilitated by an intravenous pump. Typically, the bags themselves are clear with writing on them indicating their original contents. Accordingly, at quick glance the bags or tubing do not differentiate themselves.

Health care providers and technicians must be able to identify the intravenous tubing that carries the medicaments from the bag(s) to the patient and determine their contents, whether multiple bags are connected to a patient or not. When multiple bags are connected to the manifold by an often-lengthy tube, the health care providers must know which bag is which (and which tube is connected to which bag) in order to ensure that each bag's flow is properly monitored. At times, a syringe may be used to inject an additive, such as a medication, to a bag or its tube, and this information should be apparent so the bag or tube that received the additive is identifiable, as is the additive itself. Furthermore, instructions and other information are often provided for the bags, such as when the bag was connected, how long it should be connected, and how much fluid should be delivered to the patient.

Typically, the tubes from the pumps, intravenous bags or pressure infusers are identified by adhering a tape or pressure sensitive adhesive label to the tube of the bag. With tape, many practical problems are introduced. Writing on adhesive tape can be problematic as the tape needs to be taken off a dispenser roll typically and then placed down on flat, stiff or hard writing surface so that medical personnel can legibly write on the non-adhesive surface of the tape. If not enough tape is removed for the label or the information as written takes up too much space on the tape surface, then when the tape is wrapped around the tube, that portion of the tape in contact with the tube may have writing thereon. This generally will make the writing very difficult to decipher as it too will wrap around the tube.

Some of the same concerns are present with pressure-sensitive labels, especially if they are not provided with a removable backing on their back adhesive surface. With both tape and labels, if they are wrapped unevenly or in a skewed manner so that the two portions extending away from the tube do not match there will be a sticky portion exposed which can attract dirt and bacteria, or can undesirably stick to another object. In practice, it is difficult to make legible notations on a soft label piece of tape once it is adhered to the tube. The labels also tend to be either paper or cloth which both suffer if a spilled or leaked fluid contacts the label. Adhesive from the label often remains on the tube after the label is removed, adhesive that attracts dirt and bacteria and requires labor to clean. Cleaning the tube with a solvent may cause degradation of the integrity of the tube or may introduce undesirable residual chemicals in a controlled environment such as an operating room.

In addition to intravenous infusion systems or drip bags, it is also desirable to be able to identify the fluids flowing through other tube systems. For instance, a person on a breathing apparatus may be connected to a tube providing oxygen, and/or a tube delivering gaseous anesthesia. In such a case, health care providers need to differentiate between the separate tubes or recognize what gas is being delivered by a tube.

SUMMARY OF THE INVENTION

The foregoing and other problems are overcome, and other advantages are realized, in accordance with the disclosed, alternative embodiments of these teachings.

In accordance with the present invention, a tag is provided for a fluid medicament delivery system that treats patients by intravenously infusing various types of fluids via flexible tubes extending from fluid sources such as pumps, flexible bags and/or pouches. This labeling system allows for immediate access to identifying information in situations where monitoring or modification of medicaments is required quickly in critical care situations. Alternatively, the tag can also be used for labeling any tubes, Cables, Wires, Conduits and the like, where identification with a user-friendly indicia receiving member allows for writing to be received thereon that is more easily applied and/or read versus prior adhesive-based labels or tape. Furthermore, the tube or wire receiving channel is adaptable for adherence to a tube system with minimal deformation of the tube therefore not restricting the fluid flow therein.

Preferably, the tag is a clip having a first and second section, the second section comprising a channel therein for securing a tube or wire. The channel comprises resilient support arms extending inward from the channel sides which flex inward upon the forced entry of a tube or wire into the channel. The clip first section folds over and is secured onto the clip second section, pushing the tube or wire into the channel, further flexing the resilient support arms inward with minimal deformation of the tube or cable therein. The equal and opposite forces provided by the first section contact with the tube and the resiliency of the flexible arms allow the tag to be secured to the tube or wire while at the same time allow for the tag to be moved into different positions along the length of the wire or tube. The tag has a rigid molded plastic member that provides the medical personnel or health care providers a substantially stiff or hard surface so that they can write legibly thereon.

BRIEF DESCRIPTION OF THE DRAWINGS

The foregoing aspects and other features of the present invention are explained in the following description, taken in connection with the accompanying drawings, wherein.

DETAILED DESCRIPTION OF THE PREFERRED EMBODIMENTS

When reading this section which describes exemplary embodiments, one should keep in mind several points. First, the following exemplary embodiments are what the inventor believes to be the best mode for practicing the invention at the time this patent was filed. Thus, since one of ordinary skill in the art may recognize from the following exemplary embodiments that substantially equivalent structures or substantially equivalent acts may be used to achieve the same results in exactly the same way, or to achieve the same results in a not dissimilar way, the following exemplary embodiments should not be interpreted as limiting the scope of just the embodiments described.

Second, aspects of the invention, including elements, acts, functions, and relationships (shown or described) should not be interpreted as being essential unless they are explicitly described and identified as being essential. Third, a function or an act should be interpreted as incorporating all modes of doing that function or act, unless otherwise explicitly stated (e.g., one recognizes that "tacking" may be done by nailing, stapling, gluing, hot gunning, riveting, etc., and so a use of the word tacking invokes stapling, gluing, etc., and all other modes of that word and similar words, such as "attaching"). Fourth, unless explicitly stated otherwise, conjunctive words (such as "or", "and", "including", or "comprising" for example) should be interpreted in the inclusive, not the exclusive, sense.

While certain embodiments of the present invention have been illustrated and described herein, the present invention should not be limited to such illustrations and descriptions. It should be apparent to those skilled in the art that changes and modifications may be incorporated and embodied as part of the present invention and are within the scope of the claims.

Figure 1:
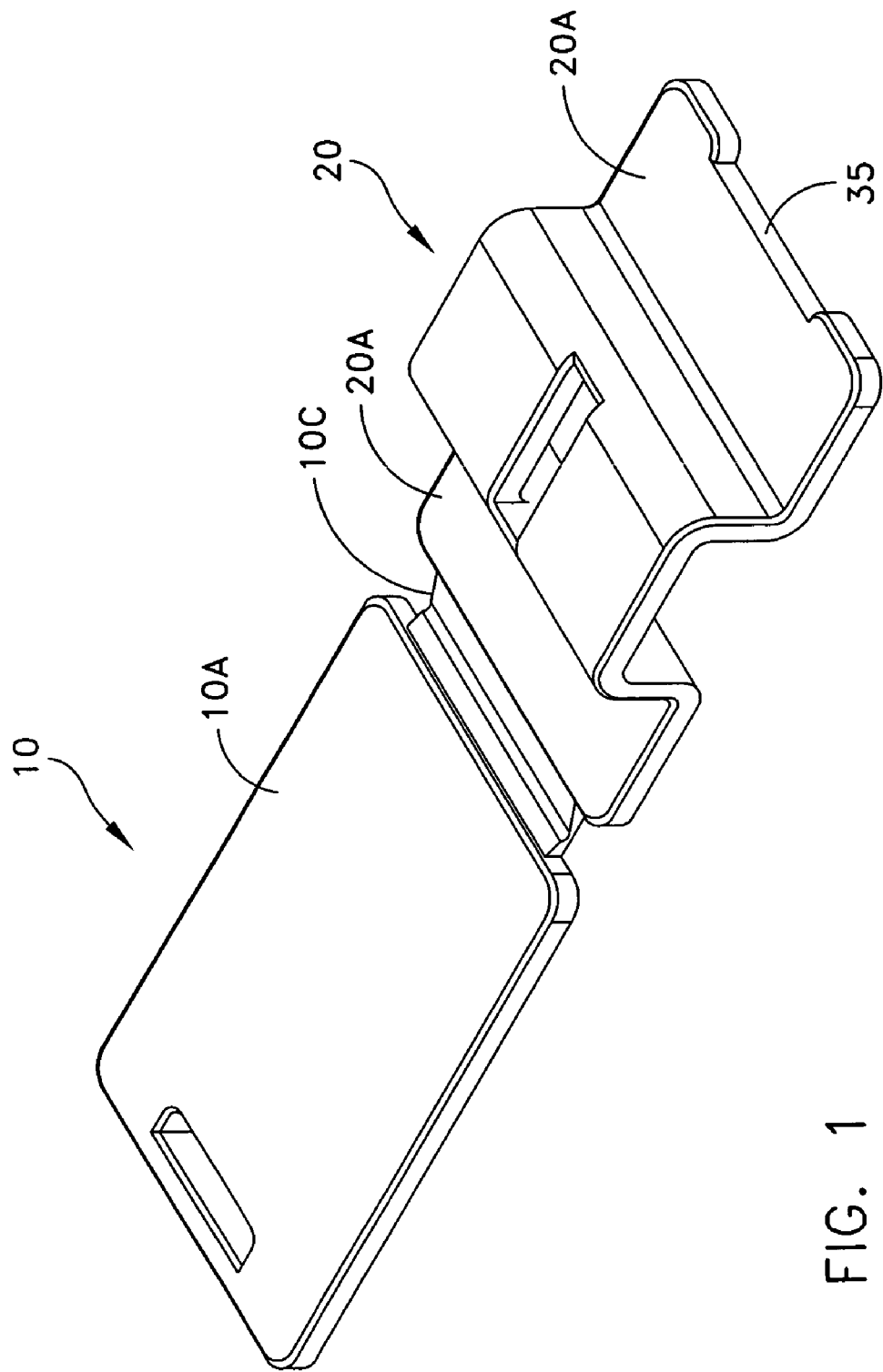
FIG. 1 is a top perspective view of the first and second sections of the tag clip of the present invention in the open position prior to being secured about a tube or cable.
Figure 4:
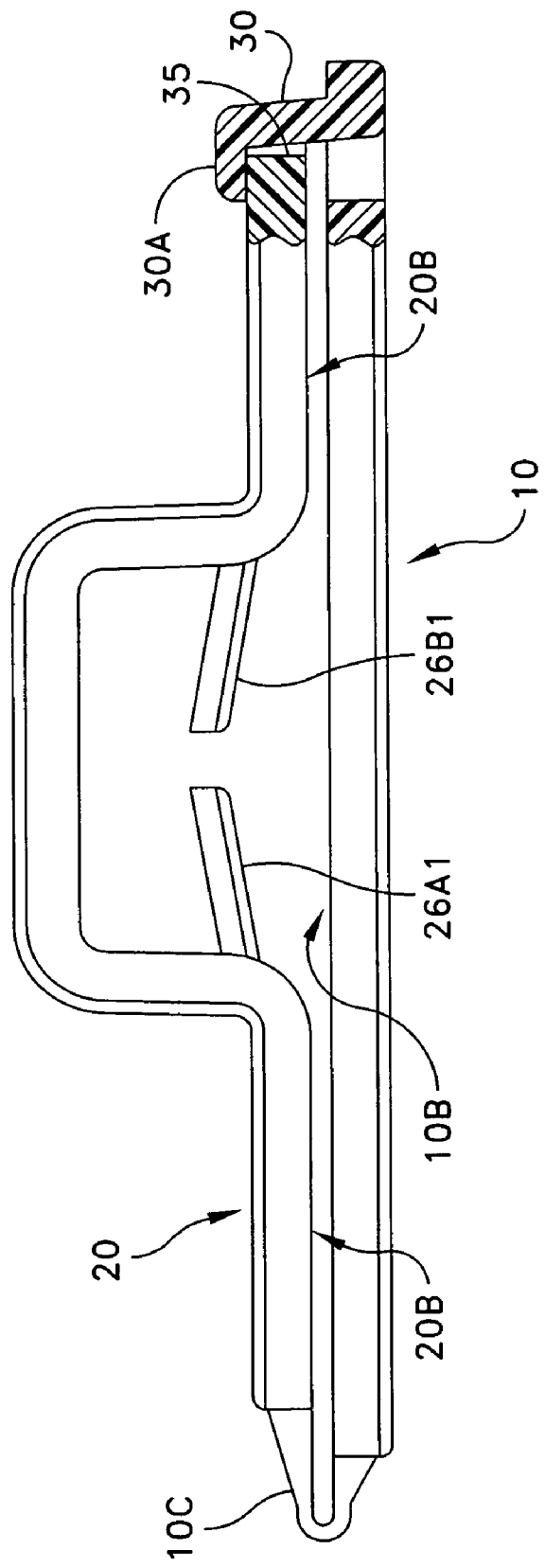
FIG. 4 is a side view of the first and second sections of the tag clip of the present invention in the closed position.
Figure 5:
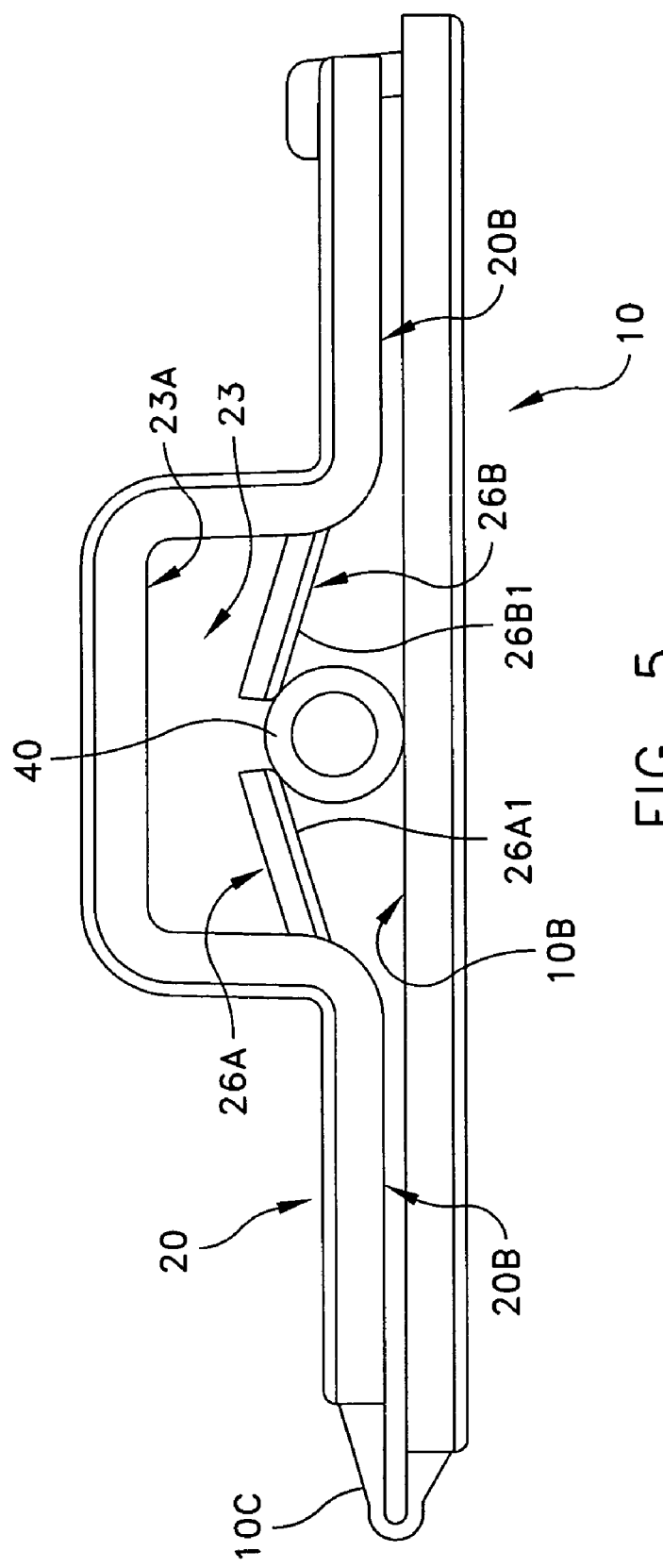
FIG. 5 is a side view of the first and second sections of the tag clip of the present invention in the closed position after being secured about a tube.
Figure 6:
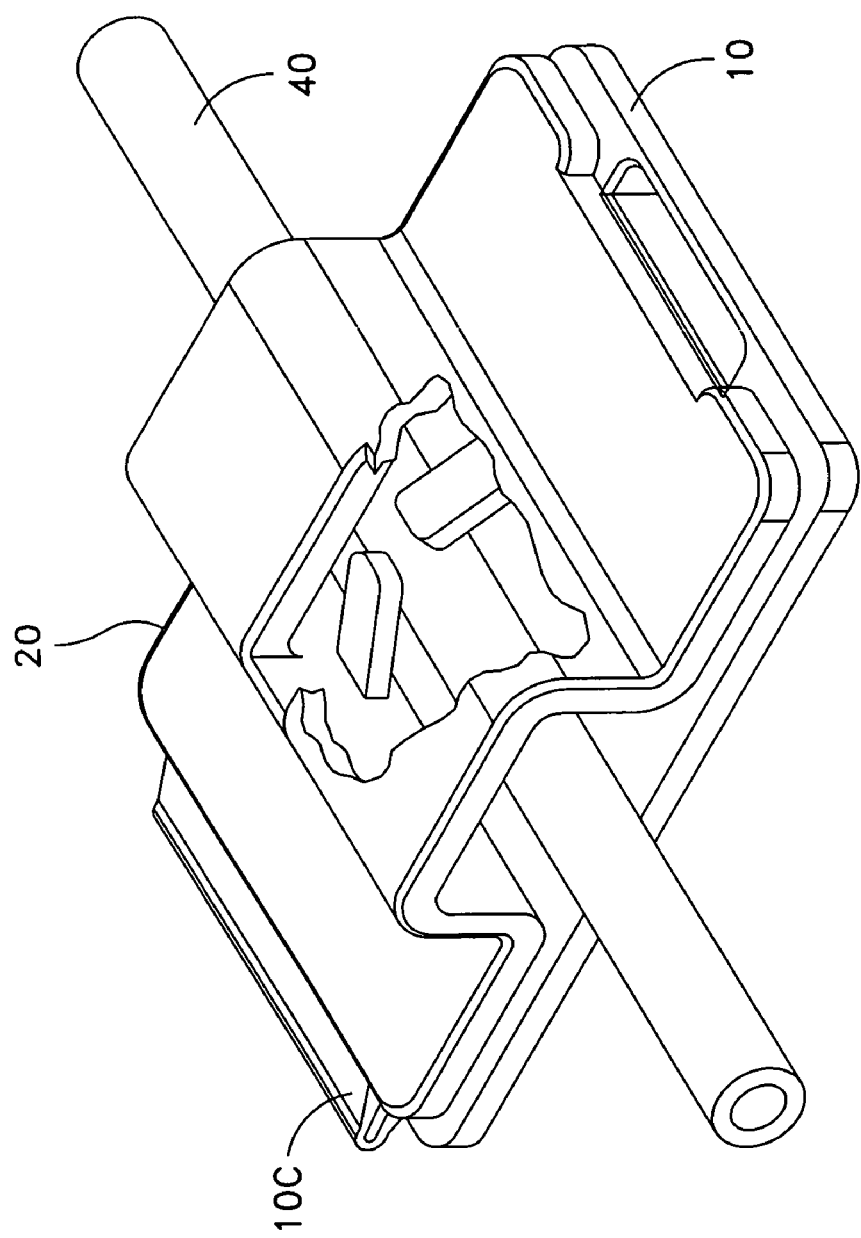
FIG. 6 is a top perspective view of FIG. 5, with a cutout illustrating a secured tube therein.

Referring to the drawings (FIGS. 1-7C) of the invention in detail, FIG. 1 illustrates an embodiment of the present invention prior to being secured to a cable or tube and separated into a first section 10 and second section 20. First section 10 includes a planer bottom face 10A and planer top face 10B and second section 20 includes a bottom face 20A and a top face 20B. In the preferred embodiment, the first and second sections are attached by a flexible attachment means 10C which allows for first section 10 to be rotated to a position substantially parallel with second section 20 as illustrated in FIGS. 4 and 5.

Planer top face 10B includes a stiffly resilient engagement extension 30 extending outward therefrom which includes a locking extension 30A. Sections 10 and 20 are locked together as illustrated in FIG. 4 when, section 10B is closed upon section 20B and extension 30A is biased outward to allow end surface 35 to slideably engage the bottom surface of locking section 30A. Locking extension 30A then flexes back to a normal position having secured end surface 35 allowing for sections 10 and 20 to remain substantially parallel to each other as illustrated in FIG. 4.

Figure 7A:
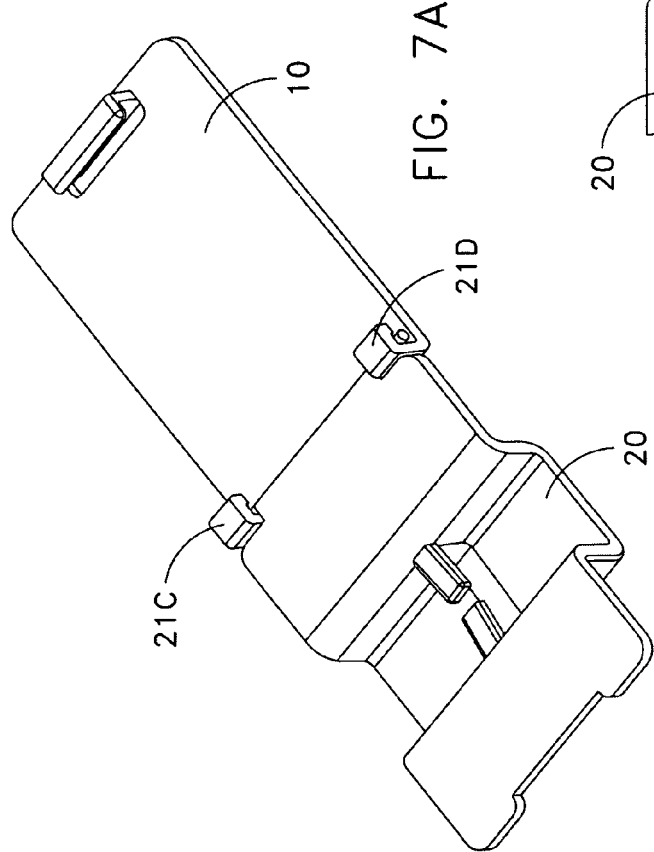
FIGS. 7A-7C illustrate alternative embodiments of the hinge attachment means.
Figure 7C:
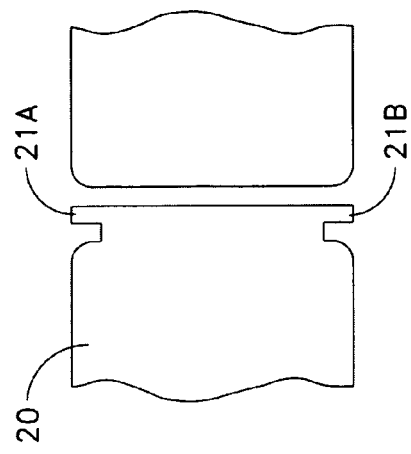
Figure 7B:
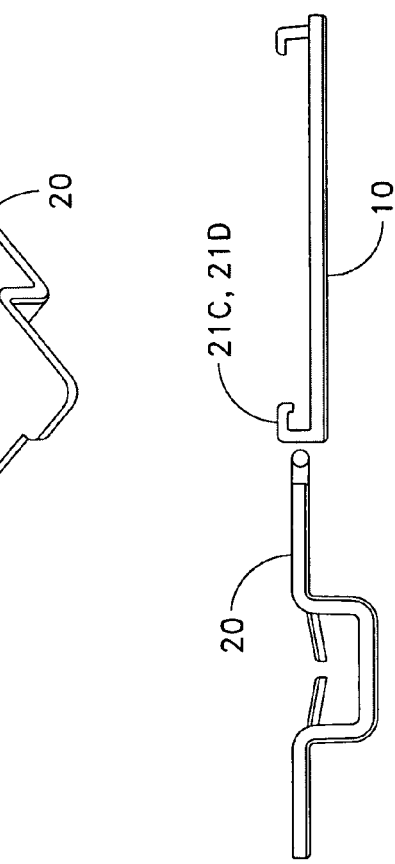

Attachment means 10C can be a thin pliable plastic, or other material or mechanism that connects first section 10 and second section 20 and which allows sections 10 and 20 to be pivoted about an axis and rotated to a parallel orientation. FIGS. 7A-7C illustrate an alternative configuration for attachment means 10C. As illustrated in FIGS. 7A-7C, section 20 includes extensions 21A and 21B, which engage and lock into end hooks 21C and 21D of section 10 (FIG. 7A, 7B). This configuration allows for section 10 to be rotated into a substantially parallel fixed position to section 20.

Figure 2:
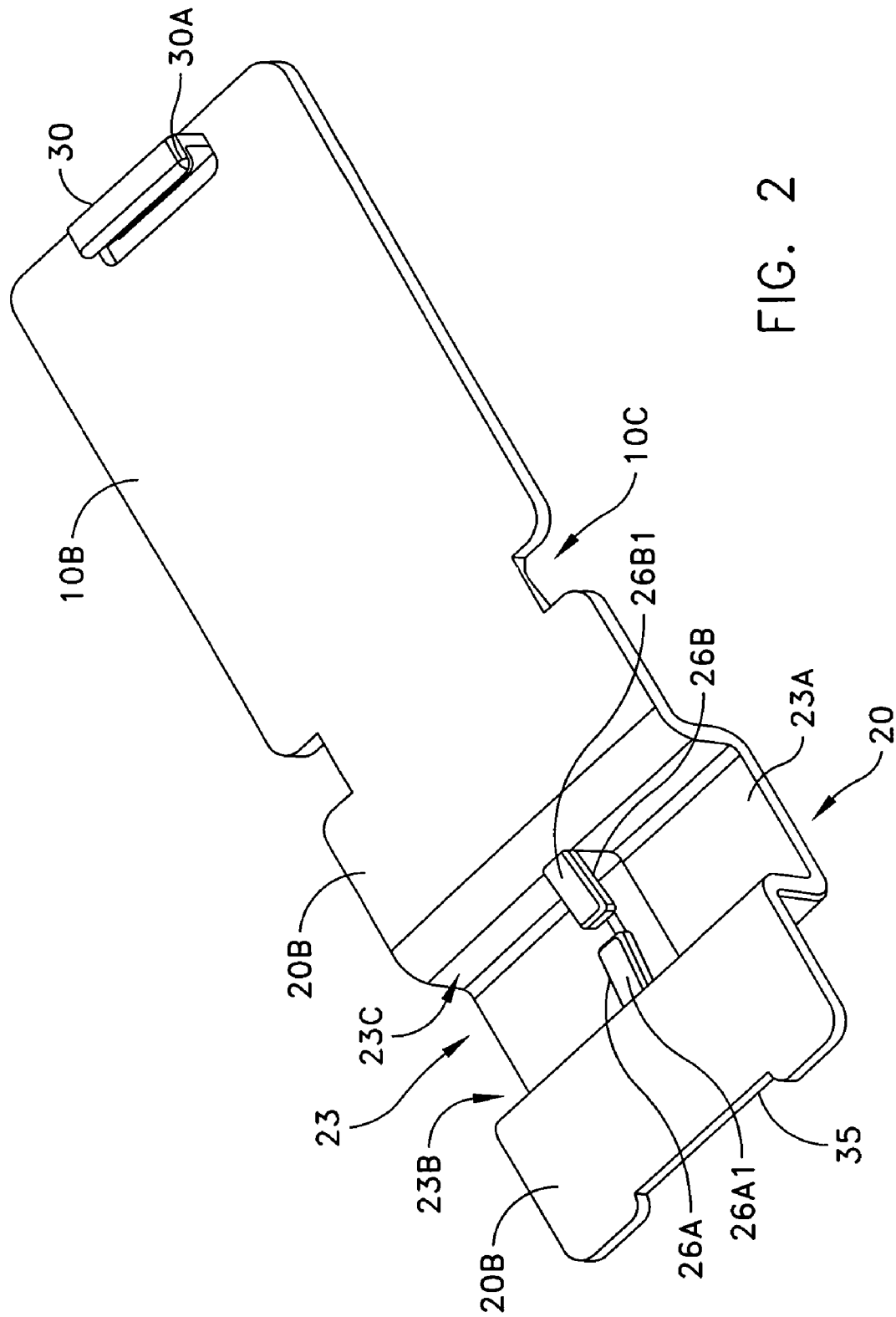
FIG. 2 is a bottom perspective view of the drawing of FIG. 1.

Referring to FIG. 2, second section 20 further includes a channel 23 having a top wall 23A, and a first and second side walls 23B and 23C. Resilient support arms 26A and 26B extend inward from first sidewall 23B and second sidewall 23C respectively. The support arms include a contact surface 26A1 and 26B1. The surface is large enough to evenly distribute forces on a tube placed thereon and secured within the channel 23 so as not to kink or puncture the tube.

Figure 3:
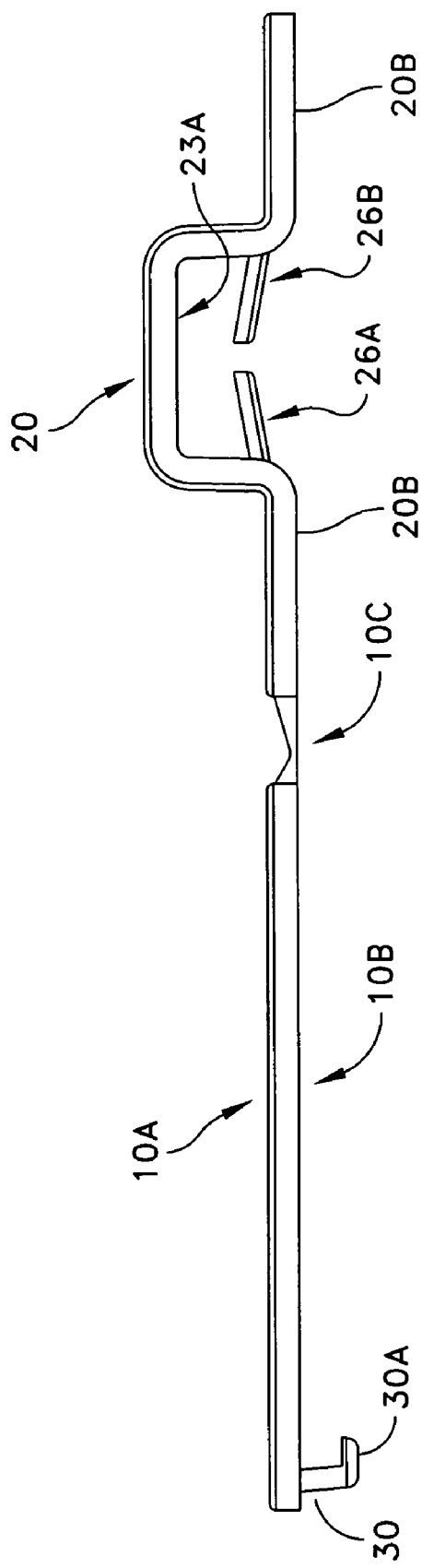
FIG. 3 is a side view of the invention of FIG. 1, with the left and right side views being identical.
Figure 3A:
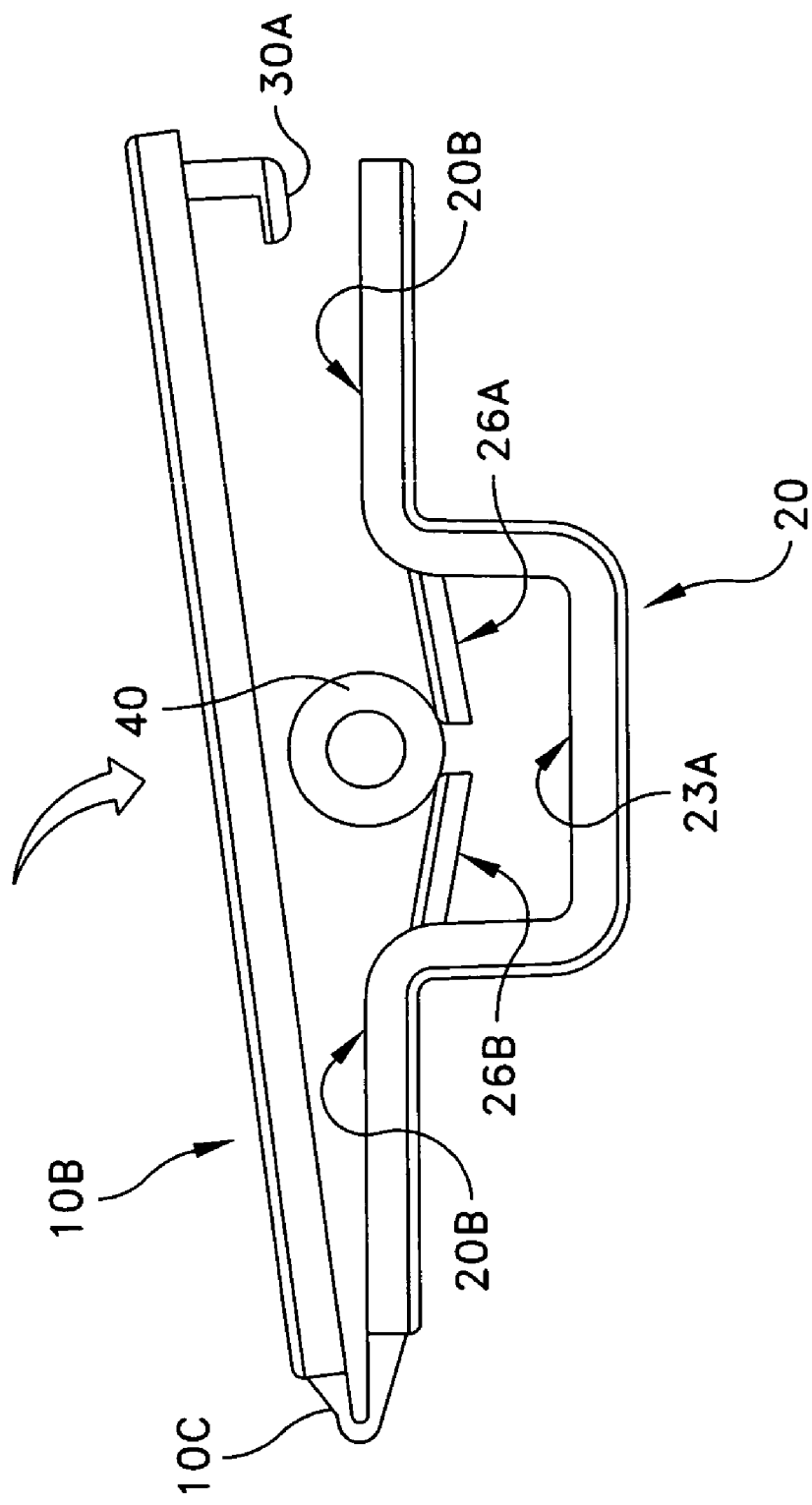

In the preferred embodiment, two arms are utilized, however, a plurality of arms may also be used. To utilize the tag clip of the present invention a tube or cable 40 is first placed within channel 23, resting on contact surfaces 26A1 and 26B1. The resilient support arms 26A and 26B are positioned such that a portion of the periphery of tube or cable 40 extends beyond top face 20B when the tube or cable 40 is placed within channel 23 as illustrated in FIG. 3A.

Furthermore, the periphery of tube or cable 40 extends beyond top face 20B sufficient to allow for planer top face 10B to exert force on tube 40 when in the closed position thereby forcing resilient support arms 26A and 26B inward towards top wall 23A as illustrated in FIG. 5. Top surface 10B contacts and forces tube or cable 40 inward while resilient support arms 26A and 26B attempt to flex back to their normal positions thereby creating equal and opposite forces securing the tag clip but allowing the clip to slide and rotate about the tube or cable 40.

Surface 10A is used as a labeling surface for tube/cable identifying information. The surface may be written on with a permanent marker or a pre-labeled sticker may be affixed thereto.

I claim:

1. A Tag Clip for labeling tubes, cables and the like comprising:
   a first section and a second section,
      wherein said first section includes a substantially planer top and bottom surface, and said second section includes a recessed center channel section, said recessed center channel section having adjacent, substantially planer side sections, said side sections having a top and bottom surface, said top surface of said first section and said top surface of said side sections substantially parallel when said first and second sections are secured,
   said recessed center channel receiving a tube or cable placed therein, said recessed center channel further including a plurality of support arms, said tube or cable in contact with said support arms, said support arms positioned within said recessed center channel such that a portion of said tube or cable contacting said support arms is positioned out of said recessed center channel,
   said first section secured relative to said second section such that a portion of said first section forces said tube or cable into said recessed center channel, said plurality of support arms flexing to allow said portion of said tube or cable positioned out of said recessed center channel to be forced into said channel, said first section and said support arms creating equal and opposite forces securing said tag clip to said tube or cable.

2. The tag clip of claim 1 wherein said recessed center channel comprises a top wall and first and second side walls, wherein said support arms extend inward from said first and second side walls.

3. The tag clip of claim 2 wherein said support arms include a contact surface, said tube or cable contacting said contact surface, said contact surface evenly distributing said first section forces so as not to kink or puncture said tube or cable.

4. The tag clip of claim 1, wherein said top surface of said first section contacts said top surface of said side sections when said first and second sections are secured.

5. The tag clip of claim 1, wherein said first section and said second section are attached by an attachment means, said attachment means allowing for said first section to be rotated to a position substantially parallel to said second section, when said first and second sections are secured.

6. The tag clip of claim 5, wherein said attachment means is a thin, pliable plastic.

7. The tag clip of claim 5, wherein said attachment means comprises a plurality of extensions extending from said second section engaged by a plurality of hooks extending from said first section.

8. The tag clip of claim 1, wherein said first section includes an engagement extension at one end, said engagement extension engaging an end surface of said second section to secure said first and second sections.

9. A Tag Clip for labeling tubes, cables and the like comprising:
   a first section comprising a substantially planer top and bottom surface, said first section having at one end an engagement extension and at the opposite end an attachment means;
   a second section attached at one end to said attachment means, said second section having a channel, said channel comprising a top wall and first and second side walls, said first and second side walls having a plurality of inwardly extending support arms, said channel being recessed, said channel having adjacent, substantially planer side sections, said side sections having a top and bottom surface, said top surface of said first section and said top surface of said side sections substantially parallel when said first and second sections are secured by said engagement extension.

10. The tag clip of claim 9, wherein said top surface of said first section contacts said top surface of said side sections when said first and second sections are secured.

* * * * *